(12) United States Patent
Kharam et al.

(10) Patent No.: US 11,478,201 B2
(45) Date of Patent: Oct. 25, 2022

(54) SYSTEMS AND METHODS FOR MONITORING PHYSIOLOGIC CHANGES USING CARDIAC ELECTROGRAM SIGNALS

(71) Applicant: Cardiac Pacemakers, Inc., St. Paul, MN (US)

(72) Inventors: Aleksandra Kharam, Maple Grove, MN (US); Ramesh Wariar, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 227 days.

(21) Appl. No.: 16/722,711

(22) Filed: Dec. 20, 2019

(65) Prior Publication Data

US 2020/0196960 A1   Jun. 25, 2020

Related U.S. Application Data

(60) Provisional application No. 62/783,888, filed on Dec. 21, 2018.

(51) Int. Cl.
  *A61B 5/00*   (2006.01)
  *A61B 5/145*  (2006.01)
  *A61B 5/352*  (2021.01)
  *A61B 5/07*   (2006.01)

(52) U.S. Cl.
  CPC ........ *A61B 5/7278* (2013.01); *A61B 5/14546* (2013.01); *A61B 5/352* (2021.01); *A61B 5/486* (2013.01); *A61B 5/6861* (2013.01); *A61B 5/076* (2013.01)

(58) Field of Classification Search
  CPC ... A61B 5/7278; A61B 5/352; A61B 5/14546; A61B 5/486; A61B 5/6861; A61B 5/076
  See application file for complete search history.

(56) References Cited

U.S. PATENT DOCUMENTS

| 9,307,921 B2 | 4/2016 | Friedman et al. |
| 9,907,478 B2 | 3/2018 | Friedman et al. |
| 2016/0256063 A1 | 9/2016 | Friedman et al. |
| 2018/0008831 A1* | 1/2018 | An ............ A61N 1/36564 |

FOREIGN PATENT DOCUMENTS

WO   WO-2017091736 A1 *  6/2017  ........... A61B 5/0205

OTHER PUBLICATIONS

Y. Yang, L. Ji and J. Wu, "Outlier detection in heart rate signal using activity information," Proceedings of the 10th World Congress on Intelligent Control and Automation, 2012, pp. 4511-4516, doi: 10.1109/WCICA.2012.6359242 (Year: 2012).*

* cited by examiner

*Primary Examiner* — Mallika D Fairchild
*Assistant Examiner* — Shreya Anjaria
(74) *Attorney, Agent, or Firm* — Pauly, DeVries Smith & Deffner LLC

(57) ABSTRACT

Various embodiment disclosed herein include a method for monitoring serum potassium in a patient. The method can include gathering cardiac electrogram data from the patient using two or more electrodes, separating the cardiac electrogram data into discrete subunits including a T-wave, aligning T-waves to create aligned discrete subunits, averaging the aligned discrete subunits to generate an average T-wave for the cardiac electrogram data, and determining a serum potassium value using the average T-wave for the cardiac electrogram data and a predetermined model relating T-wave values with serum potassium magnitudes.

20 Claims, 15 Drawing Sheets

SYSTEMS AND METHODS FOR MONITORING PHYSIOLOGIC CHANGES USING CARDIAC ELECTROGRAM SIGNALS

This application claims the benefit of U.S. Provisional Application No. 62/783,888, filed Dec. 21, 2018, the content of which is herein incorporated by reference in its entirety.

FIELD

Embodiments herein relate to systems and methods for monitoring physiologic changes with cardiac electrocardiogram signals.

BACKGROUND

In the context of diagnosis and monitoring of patients, clinicians frequently evaluate many different elements of data about their patients including physical observations, descriptions of symptoms, test results, and the like. One aspect that testing can reveal is the physiological concentration of electrolytes for the patient. Electrolyte concentrations can be important to know because of their effect on various organs and bodily functions.

Hyperkalemia and hypokalemia are common in patients with a variety of disease states such as heart failure, chronic kidney disease and diabetes mellitus. It is also prevalent with use of diuretic medications and RAAS inhibitors. Traditional methods of monitoring potassium levels require blood sampling, which can be difficult for numerous reasons.

SUMMARY

Aspects herein relate to monitoring physiologic changes using cardiac electrogram signals. In a first aspect a method for monitoring serum potassium in a patient comprises gathering cardiac electrogram data from the patient using two or more electrodes; separating the cardiac electrogram data into discrete subunits including a T-wave; aligning T-waves to create aligned discrete subunits; averaging the aligned discrete subunits to generate an average T-wave for the cardiac electrogram data; and determining a serum potassium value using the average T-wave for the cardiac electrogram data and a predetermined model relating T-wave values with serum potassium magnitudes.

In a second aspect, in addition to one or more of the preceding or following aspects, or in the alternative to some aspects, determining a serum potassium value using the average T-wave for the cardiac electrogram data and a predetermined model relating T-wave morphology with serum potassium values comprises calculating an average T-wave change of the patient by comparing the average T-wave for the cardiac electrogram data against a previously determined baseline average T-wave for the patient; and determining a serum potassium value using the average T-wave change for the cardiac electrogram data and a predetermined model relating T-wave change values with serum potassium values.

In a third aspect, in addition to one or more of the preceding or following aspects, or in the alternative to some aspects, the method comprising periodically updating the model by evaluating an average T-wave of the patient corresponding to a serum potassium concentration of the patient measured in vitro.

In a fourth aspect, in addition to one or more of the preceding or following aspects, or in the alternative to some aspects, the model is only updated after at least two separate in vitro measurements are made.

In a fifth aspect, in addition to one or more of the preceding or following aspects, or in the alternative to some aspects, the model is only updated after at 21 days after a device implant.

In a sixth aspect, in addition to one or more of the preceding or following aspects, or in the alternative to some aspects, gathering cardiac electrogram data from the patient using two or more electrodes is performed with an implanted device.

In a seventh aspect, in addition to one or more of the preceding or following aspects, or in the alternative to some aspects, the model relating T-wave values with serum potassium values represents the output of at least one of a regression analysis and a machine learning analysis.

In an eighth aspect, in addition to one or more of the preceding or following aspects, or in the alternative to some aspects, the inputs for the regression analysis or machine learning analysis include previous cardiac electrogram data for the patient.

In a ninth aspect, in addition to one or more of the preceding or following aspects, or in the alternative to some aspects, each discrete subunit including a T-wave comprises cardiac electrogram data spanning a time span of at least 0.15 seconds.

In a tenth aspect, in addition to one or more of the preceding or following aspects, or in the alternative to some aspects, each discrete subunit including a T-wave comprises cardiac electrogram data spanning a time span that is user programmable.

In an eleventh aspect, in addition to one or more of the preceding or following aspects, or in the alternative to some aspects, the number of discrete subunits that are averaged is at least about 10 subunits.

In a twelfth aspect, in addition to one or more of the preceding or following aspects, or in the alternative to some aspects, the cardiac electrogram data spans at least 10 minutes.

In a thirteenth aspect, in addition to one or more of the preceding or following aspects, or in the alternative to some aspects, aligning T-waves is selected from the group consisting of aligning peaks of the T-waves, aligning starting points of the T-waves, aligning ending points of the T-waves, aligning midpoints of the T-waves, aligning a single point of the T-waves, or aligning two or more points of the T-waves.

In a fourteenth aspect, in addition to one or more of the preceding or following aspects, or in the alternative to some aspects, discarding discrete subunits representing statistical outliers.

In a fifteenth aspect, in addition to one or more of the preceding or following aspects, or in the alternative to some aspects, statistical outliers are evaluated by evaluating at least one of R to R variability and R to T variability.

In a sixteenth aspect, in addition to one or more of the preceding or following aspects, or in the alternative to some aspects, further comprising prompting the patient to take a specific action prior to gathering cardiac electrogram data from the patient.

In a seventeenth aspect, in addition to one or more of the preceding or following aspects, or in the alternative to some aspects, gathering cardiac electrogram data from the patient starts based on at least one of the patient assuming a particular posture, a particular time of day, or activity below a predefined threshold.

In an eighteenth aspect, in addition to one or more of the preceding or following aspects, or in the alternative to some aspects, the method further comprising storing a new baseline T-wave value of the patient if the T-wave is stable over at least a threshold period of time.

In a nineteenth aspect, in addition to one or more of the preceding or following aspects, or in the alternative to some aspects, the threshold period of time comprising at least 30 days.

In a twentieth aspect, in addition to one or more of the preceding or following aspects, or in the alternative to some aspects, an implantable medical device comprising: a housing; a control circuit disposed in the housing; an electric field sensor channel interface in electrical communication with the control circuit; wherein the control circuit is configured to separate cardiac electrogram data received from the electric field sensor into discrete subunits including a T-wave; align the subunits using the T-waves thereof to create aligned discrete subunits; average the aligned discrete subunits to generate an average T-wave for the cardiac electrogram data; and determine a serum potassium value using the average T-wave for the cardiac electrogram data and a predetermined model relating T-wave values with serum potassium values.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
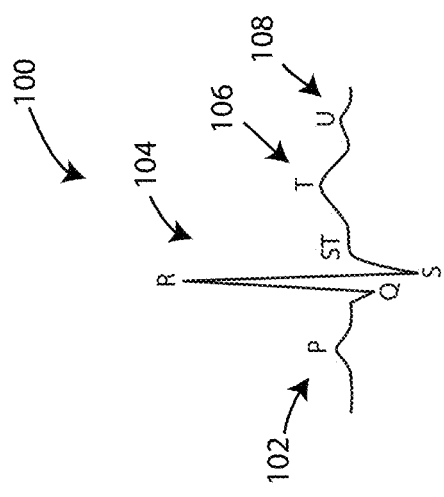
FIG. 1 is a schematic diagram of a cardiac electrogram wave in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Electrolyte concentrations are clinically important because of their effect on various organs and bodily functions. Typically, electrolyte concentrations are assessed by drawing a fluid sample (or other sample) from the patient followed by conducting an in vitro assay on the sample. Changes in potassium levels can happen in the span of hours, making fluid draws ineffective for monitoring potassium levels on a continuous basis.

Potassium concentration can impact cardiac repolarization and therefore the morphology of the cardiac electrogram, such as the T-wave. Methods and systems disclosed herein estimate potassium levels using cardiac electrogram data, such as the T-wave. The systems and methods disclosed herein can account for variations in the cardiac electrogram data, which commonly occur with disease progression and potential changes in the estimation coefficients. As used herein, the term "cardiac electrogram data" shall include ECG data (including but not limited to surface electrogram (ECG) vectors), cardiac electrogram data gathered with implanted electrodes, intracardiac electrogram data obtained from implanted pacemaker/defibrillator leads where the T-wave corresponds to atrial/ventricular repolarization, or any other data reflecting electrical activity of the heart including a T-wave or a combination of one or more of a P-wave, a QRS complex, a T-wave, and a U-wave. As used herein, the term "T wave" represents the electrical activity produced by ventricular repolarization and/or atrial repolarization, unless the context dictates otherwise.

Various embodiments herein include a patient-specific and time-variant system for potassium level estimation. Cardiac electrogram data can be obtained and portions or subunits thereof including T-wave can be isolated. The portions or subunits of the cardiac electrogram data can then be processed including aligning them with one another and then averaging them to obtain an average T-wave representing the patient's condition at a particular point (or period) in time. The average T-wave (and/or a "T-wave delta" value representing the difference between the average T-wave and some baseline T-wave value) can then be sampled and evaluated using a mathematical model, function or equation that converts the T-wave morphology and/or parameters into estimated potassium levels for the patient.

The model, function or equation used can, in a starting state, be generated or obtained in various ways. In some embodiments, the model, function or equation can be a starting default model, function or equation that can be downloaded into the system or device. The default can be a universal default model, function or equation or can be a default for patients that are similar to the patient in question (in terms of various factors such as age, gender, health condition/status, or the like).

In some embodiments, the model, function or equation can be generated (using various techniques such as regression analysis described in greater detail below) from data using measurements of average T-waves of the patient matched against definitive measurements of potassium levels (via an in vitro assay or other definitive analytical testing). For example, cardiac electrogram data can be gathered from the patient using an implanted device or via electrical signals with electrode on the skin from the patient as well as a fluid sample, such as a blood sample. The potassium levels of the fluid sample can be measured (via an in vitro assay or other definitive analytical testing) and matched to an averaged T-wave of the cardiac electrogram data taken at the same time period to provide data pairing an average T-wave and a known potassium level.

These paired data sets (average T-wave and trusted potassium levels) can be generated over a period of time, such as would be the case with additional data being gathered during office visits the patient may have with care providers. In some cases, such as where only data from the individual patient is used to build the model, function or equation, the potassium estimation features herein may be not be used for a period of time until enough data is gathered from the specific patient in order to generate the model, function or equation.

In some embodiments, a hybrid approach can be used in that a default model, function or equation could be used initially and then modified based on initial data gathered for the specific patient to result in a usable model, function or equation to start.

Regardless, the model, function or equation used can be modified over time in various embodiments herein. For example, in some embodiments, the model, function or equation can be modified such as whenever a known potassium level is established and can be paired with an averaged T-wave at the same time. This updated data can be used to modify the preexisting model, function or equation to make it responsive to changes that may be occurring with the patient over time.

Gathering Cardiac Electrogram Data

Referring now to FIG. 1 a schematic of a period of a cardiac electrogram wave 100 is shown in accordance with various embodiments herein. A period of a cardiac electrogram wave 100 can include a P-wave 102, a QRS complex 104, a T-wave 106, and a U-wave 108. Each period of a cardiac electrogram wave can represent one heartbeat.

In some embodiments, the measured cardiac electrogram wave can include a plurality of P-waves, QRS complexes, T-waves, and U-waves, such as when multiple heartbeats are observed.

In some embodiments, the cardiac electrogram wave or cardiac electrogram data can be gathered from a patient using two or more electrodes, such as electrodes that are implanted within the patient or placed on the patient. In some embodiments, the cardiac electrogram data can be gathered using an implanted device. In some embodiments, implanted devices may have electrodes located within the body in a variety of locations such as subcutaneous, submuscular, and intracardiac. For example, intracardiac electrograms may be captured from leads located in the atria or ventricles using different electrode/vector spacings (e.g.

unipolar or bipolar). However, in some embodiments, the cardiac electrogram data can also be gathered using an external device connected to electrodes on the patient's skin.

In some embodiments, the patient can be prompted to take a specific action prior to gathering the cardiac electrogram data, such as to ensure the captured cardiac electrogram data is accurate or consistent with previous assessments. In some embodiments, the patient can be prompted to assume a semi-recumbent position, such as in a chair. In other embodiments, the patient can be prompted to stand or remain stationary.

In some embodiments, the cardiac electrogram data can be gathered based on an occurrence of an event, such as that patient assuming a particular posture, a particular time of the day, or activity of the patient falling below or above a predefined threshold.

Separating Cardiac Electrogram Data into Discrete Subunits

Figure 2:
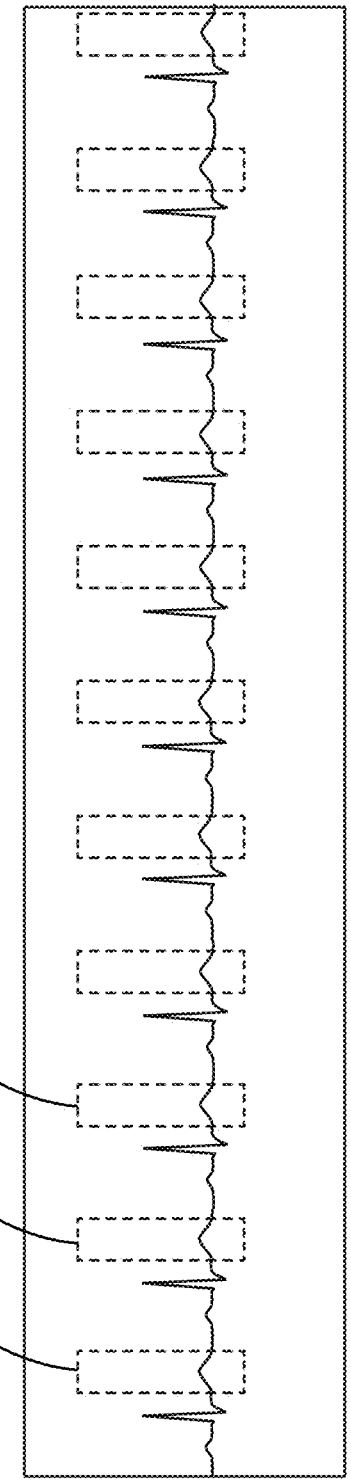
FIG. 2 is a schematic diagram of cardiac electrogram waves in accordance with various embodiments herein.

In reference now to FIG. 2, cardiac electrogram data 210 is shown in accordance with various embodiments herein, cardiac electrogram data 210 can include a plurality of periods of cardiac electrogram waves 100. As mentioned above, each period of the cardiac electrogram wave can include a P-wave 102, a QRS complex 104, a T-wave 106, and a U-wave 108. Intracardiac electrograms can include depolarization and repolarization waves.

In various embodiments, the methods and systems described herein can include separating the cardiac electrogram data into discrete subunits 212. Each of the discrete subunits 212 can include a T-wave 106. In some embodiments, each of the discrete subunits 212 can begin before the start of a T-wave 106 and stop after the end of the T-wave 106 (e.g., capturing more than the entire T-wave). In some embodiments, each of the discrete subunits 212 can begin at the start of a T-wave 106 and stop at the end of the T-wave 106 (e.g., capturing the entire T-wave). In some embodiments, each of the discrete subunits 212 can begin sometime after the start of a T-wave 106 and stop sometime before the end of the T-wave 106 (e.g., capturing less than the entire T-wave).

In some embodiments, only a portion of the cardiac electrogram data 210 is included within the subunits, such that there can be portions of the cardiac electrogram data 210 that is not included within a subunit. In some embodiments, the portions of the cardiac electrogram data 210 that is not included within one of the subunits 212 can be discarded or not used in further calculations or estimates.

The subunits 212 can be divided in various manners including, but not limited to, based on specific timing, based on the identification of specific features (such as particular waves, peaks, valleys, plateaus, magnitudes, slopes, etc.), or a combination thereof. In some embodiments, the subunits 212 can be divided based detecting U waves and QR complexes and taking the data (or a portion thereof such as that covering a specific time span) in between. In some embodiments, each discrete subunit can include cardiac electrogram data spanning a specific time span. In some embodiments, the time span can be user programmable, such that a clinician or other user can enter a length of time for the time span. In some embodiments, the time span can be at least 0.05 second, 0.10 seconds, 0.15 seconds, 0.20 seconds, 0.25 seconds, 0.30 seconds, 0.35 seconds, or 0.40 seconds. In some embodiments, the time span can be no longer than 1 second, 0.75 seconds, 0.50 seconds, 0.40 seconds, or 0.30 seconds. Some embodiments can include a range falling within one of the upper bounds and one of the lower bounds listed herein. Cardiac electrogram data can be divided into depolarization and repolarization subunits.

Aligning T-Wave Subunits

Figure 3:
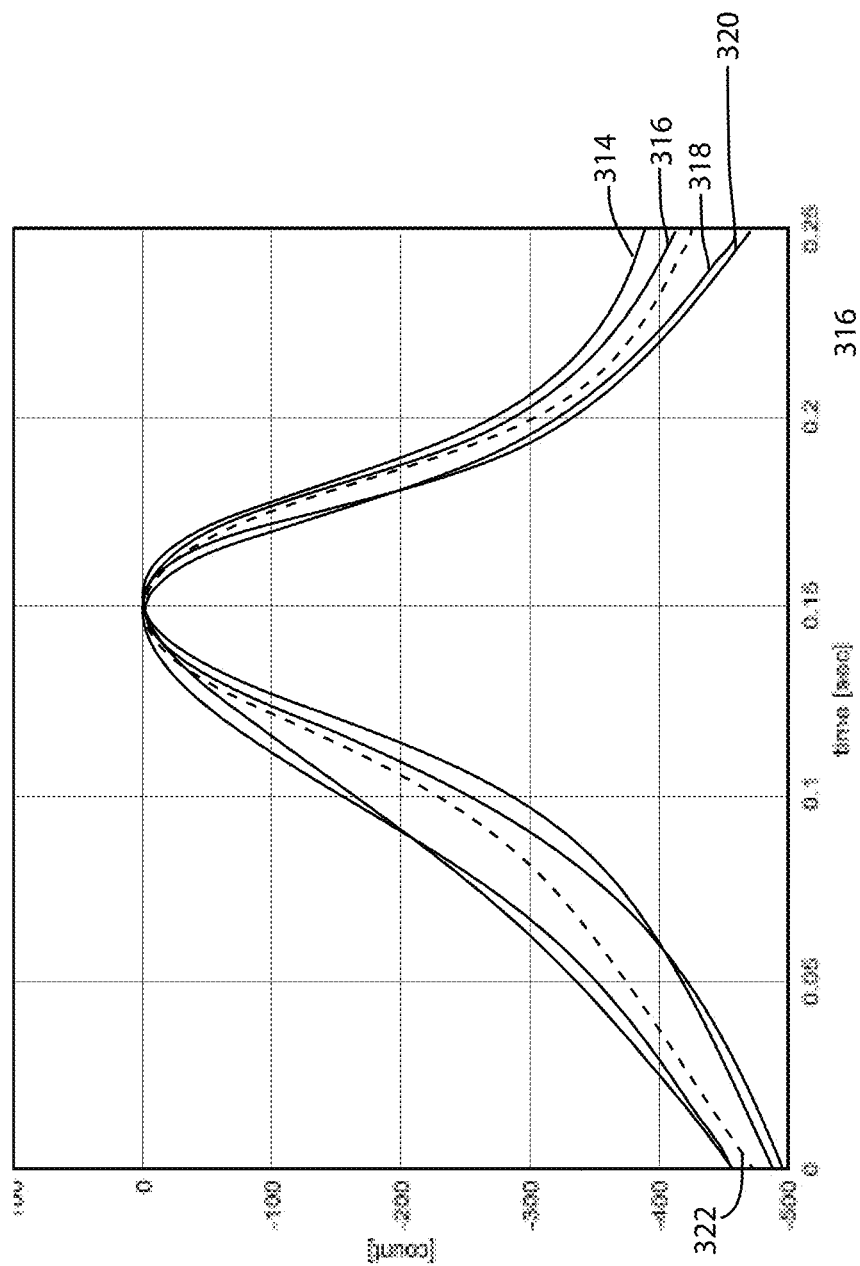
FIG. 3 is a schematic diagram of an averaged wave in accordance with various embodiments herein.

In reference now to FIG. 3, a schematic diagram is shown of aligned T-waves in accordance with various embodiments herein. In an embodiment the subunits 212 including T-waves 106 can be aligned, such as to allow the T-waves 106 of subunits 212 to be averaged. FIG. 3 can represent a plurality of gathered or sensed T-waves 314, 316, 318, 320 that have been aligned to determine an average T-wave 322. The average T-wave 322 can represent a current status of the patient, since the average T-wave can include only the average of subunits of recently gathered cardiac electrogram data, such as when calculating or estimating the current potassium levels in the serum of the patient.

In various embodiments, the methods and systems can include aligning T-waves to create aligned discrete subunits, such as shown in FIG. 3. In some embodiments, aligning the T-waves can include aligning the peak of each T-wave. In some embodiments, aligning the T-waves can include aligning the starting point of each T-wave. In some embodiments, aligning the T-waves can include aligning the ending point of each T-wave. In some embodiments, aligning the T-waves can include aligning a point of each of T-wave, such as a midpoint, an inflection point, a point of maximum slope, a point of minimum slope, or a point of zero slope. In some embodiments, aligning the T-waves can include aligning a midpoint of each of T-wave, such as a point that is equal distance between the starting point and the ending point. In some embodiments, aligning the T-waves can include aligning two or more points of each T-wave, such as the point of maximum slope and the point of minimum slope. In other embodiments, the repolarization subunits of the intracardiac electrograms are aligned.

Averaging Aligned Subunits

In various embodiments, the methods and systems can include averaging the aligned discrete subunits to generate an average T-wave 322 for the cardiac electrogram data 210. Similarly, for intracardiac electrograms, an average repolarization wave is generated. The average T-wave 322 can be used to determine a change of serum potassium by comparing the average T-wave 322 to a predetermined model or baseline relating T-wave morphology or shape with serum potassium magnitudes.

In various embodiments, cardiac electrogram data 210, such as data that can be used to determine an average, can include at least 5 subunits 212, at least 10 subunits 212, at least 15 subunits 212, at least 20 subunits 212, at least 25 subunits 212, at least 30 subunits 212, at least 40 subunits 212, at least 50 subunits 212, at least 75 subunits 212, or at least 100 subunits 212.

In some embodiments, the methods and systems can include discarding discrete subunits 212 that represent statistical outliers from the average T-wave. In some embodiments, the statistical outliers can be evaluated or determined by evaluating at least one of R to R variability or R to T variability. In some cases, statistical outliers can represent data that is not representative of the average state of the patient. For example, a reading can be influenced by the location of an electrode not being secured or other outside influences. As such, these subunits 212 can be discarded from the average T-wave calculation to determine a more realistic or accurate average T-wave.

In various embodiments, the cardiac electrogram data 210 comprising the subunits 212 can span at least 1 minute, at least 5 minutes, at least 10 minutes, at least 30 minutes, at least 60 minutes, at least 180 minutes, or at least 6 hours. In various embodiments, the cardiac electrogram data 210 comprising subunits 212 can span no more than 24 hours, 12 hours, 6 hours, 3 hours, or 1 hour. Some embodiments can include a range falling within one of the upper bounds and one of the lower bounds listed herein.

Normalization and Model, Function, or Equation Generation

In some embodiments, a normalization can be performed. By way of example, it can be appreciated that absolute values for the magnitude of various features of the cardiac electrogram data (including but not limited to the T-wave peak) may vary somewhat across different patients, across different times, across different electrodes or equipment used to gather the data, etc. As such, in some embodiments, the data can be normalized before it is used to generate (in whole or in part) a model, function, or equation. Many different techniques can be used for normalization. In some embodiments, normalization can occur by adjusting magnitudes of cardiac electrogram subunits (or averaged cardiac electrogram subunits) in an amount so that the peaks of all T-waves have the same magnitude. In other embodiments, the signal may be normalized to the signal intensity (e.g., root mean square value) or power.

Figure 4:
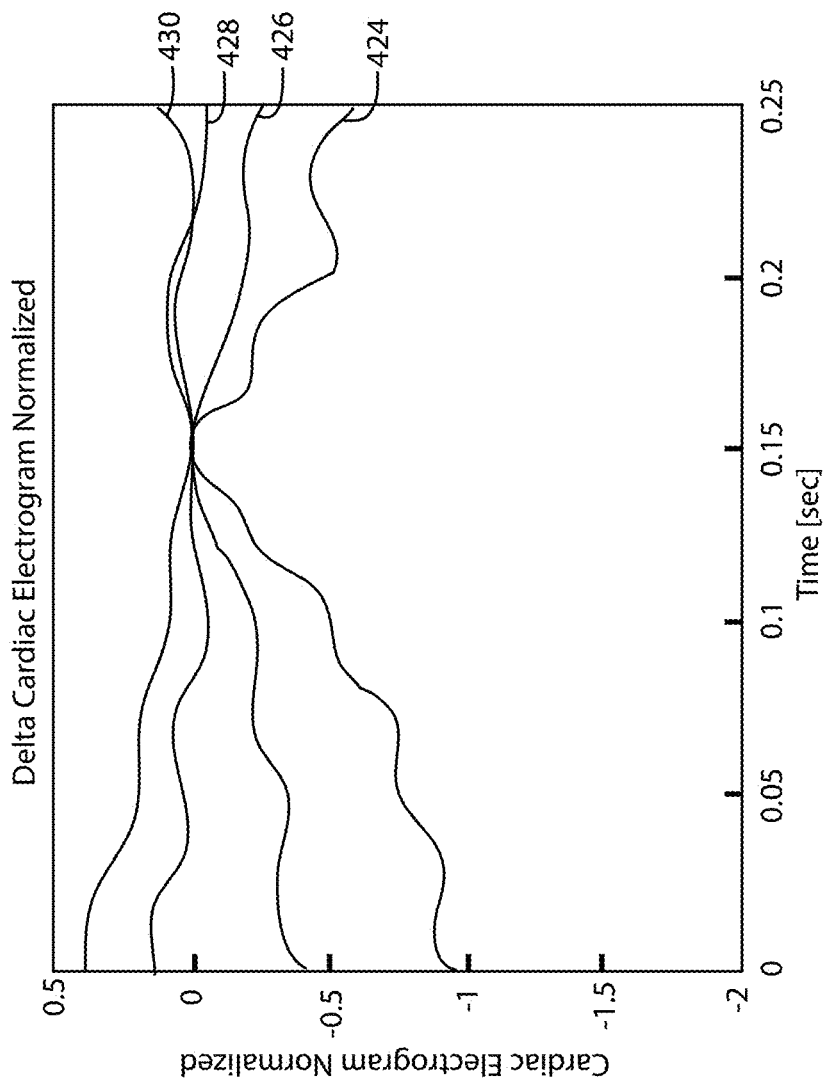
FIG. 4 is a schematic diagram of normalized cardiac electrogram waves in accordance with various embodiments herein.

FIG. 4 shows a schematic of normalized T-waves 424, 426, 428, 430 in accordance with various embodiments herein. The T-waves 314, 316, 318, 320 can be aligned as shown in FIG. 3. Once the T-waves are aligned, the T-waves can be normalized, such as shown in FIG. 4. The normalized T-waves 424, 426, 428, 430 can be used to determine the average T-wave 322, such as shown in FIG. 3. In other embodiments, normalized T-waves can be used to establish a baseline (such as where the use of T-wave delta values are used herein). In some embodiments, the baseline is established using only that patient's own data. In some embodiments, the baseline is established using data from a pool of patients, in addition to using the patient's own data or instead of using the patient's own data.

A model, function, or equation that relates averaged T-wave values and/or T-wave delta values to estimated potassium concentrations can be calculated or otherwise generated in various ways. By way of example, in various embodiments, a regression analysis can be performed. Regression analysis is a statistical method that can be used to characterize the relationship between two or more variables of interest. In various embodiments, the regression analysis can include ordinary least squares regression, linear regression, nonlinear regression, Bayesian linear regression, percentage regression, least absolute deviations regression, nonparametric regression, as well as other regression methods. In some embodiments, a machine learning analysis can be performed. Various other techniques can also be used to derive a model, function or equation that relates T-wave morphologies or parameters, or T-wave delta values and potassium concentrations.

T-Wave Delta and Baseline Values

As referenced above, the average T-wave and/or a "T-wave delta" value representing the difference between the average T-wave and some baseline T-wave value can be sampled and evaluated using a model, function or equation that converts the T-wave morphology and/or parameters thereof into estimated potassium levels for the patient. In embodiments where a T-wave delta approach is used, the baseline T-wave value can be set at juncture where a known potassium level is established and can be paired with an averaged T-wave at the same time. For example, such a baseline value could be set at an initial visit with a care provider. As another example, such a baseline value could be set or reset at a follow-up visit or at another time when desired by a care provider.

In some embodiments, the methods and systems can include calculating an average T-wave change of the patient by comparing the average T-wave for the cardiac electrogram data against a previously determined baseline average T-wave for the patient. In some embodiments, such a change can be determined continuously across the entire subunit and in other embodiments, such a change can be determined just at one or more specific points within the subunit.

Figure 5:
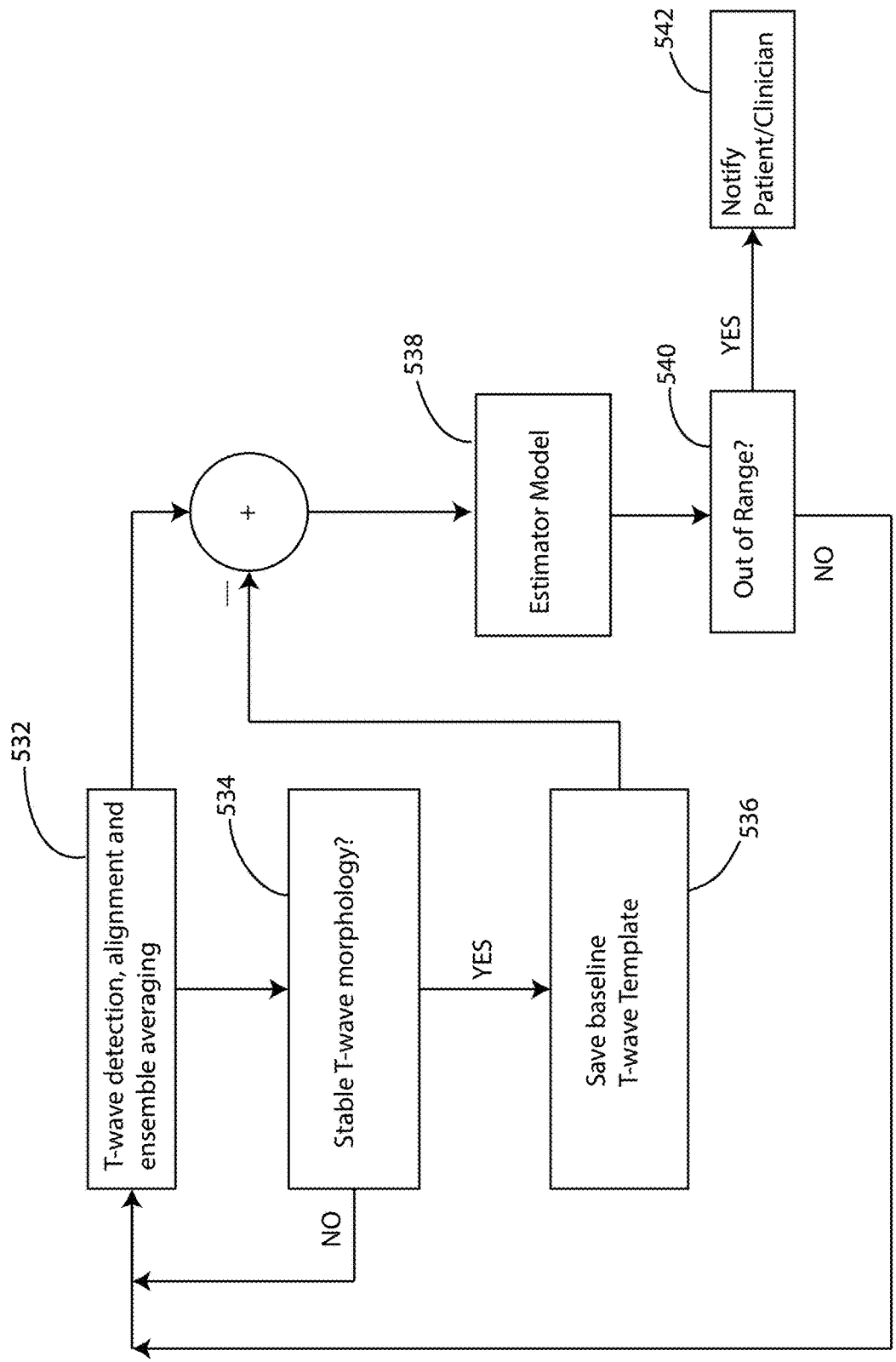
FIG. 5 is a flow chart of operations executed by a system in accordance with various embodiments herein.

FIG. 5 shows a flow chart of operations that can be executed by a system in accordance with various embodiments herein. Various embodiments of the systems and methods described herein can include operations of capturing cardiac electrogram wave data, dividing the data into T-wave containing subunits, aligning the subunits and averaging them 532.

In some instances, the T-wave can exhibit an unstable morphology due to various reasons other than changes in potassium levels. For example, in some cases, such as when the electrodes are implanted into a patient, the tissue around the electrode can require a healing period due to the trauma of the surgery. During this healing period the electrodes can be inadvertently moved or disrupted which can result in unstable T-wave morphology.

However, waiting for observed T-wave morphologies to be stable over a period of time can prevent reliance upon unstable T-wave morphologies and therefore increase accuracy. In some embodiments, the systems and methods herein can then include assessing if there is a stable T-wave morphology for a period of time 534. The period of time can be of various lengths such as a stable T-wave for at least 1, 2, 3, 7, 14, 21, or 30 days, or a length of time falling within a range between any of the foregoing.

Once the T-wave has been stable, a baseline T-wave can be established along with a measured potassium level, such as through an in vitro assay. The baseline can be saved 536.

After the baseline has been established and saved, additional cardiac electrogram data can be captured 532, such as cardiac electrogram data that represents the current physiological condition of the patient. In some embodiments, the additional cardiac electrogram data can be captured at least 1, 2, 3, 5, 7, 14, 21, 30, 45, 60, 90, 120, 180, 365 days, or longer after the baseline has been established.

The captured cardiac electrogram data can be compared with the baseline value to generate T-wave delta (change) values that can then be run through the estimator model, function or equation to result in an estimated potassium concentration and/or a change in potassium concentration with respect to the baseline value.

In some embodiments, the change in potassium can be compared to a threshold change of potassium 540. If the change in potassium is below the threshold change of potassium, the system can repeat itself by once again gathering cardiac electrogram data (continue normal operation).

However, if the change in potassium exceeds a threshold value for a change in potassium, a clinician or care provider can be notified 542. The clinician can then determine whether the change in potassium exceeded the threshold because of a change in the health status of the patient or due to an error in the estimator model. In some embodiments, additional testing, such as an in vitro assay, can be conducted to accurately quantify the actual change in potassium concentration.

If the change in potassium level is a result of an error of the estimator model, the clinician can require the model, function or equation (or coefficients thereof) to be updated, such as based on updated in vitro assay results, or entirely regenerated. In some embodiments, the estimator model, function or equation is only updated after at least two separate in vitro measurements are made. In some embodiments, the estimator model is only updated after at least three, four, five, or ten separate in vitro measurements are made. In some embodiments, the estimator model is only updated after at least 7 days, 14 days, 21 days, 28 days, 30 days, or 60 days after a device is implanted, such as to ensure the readings are stable, as discussed above.

Model, Function, or Equation Change Over Time

Figure 6A:
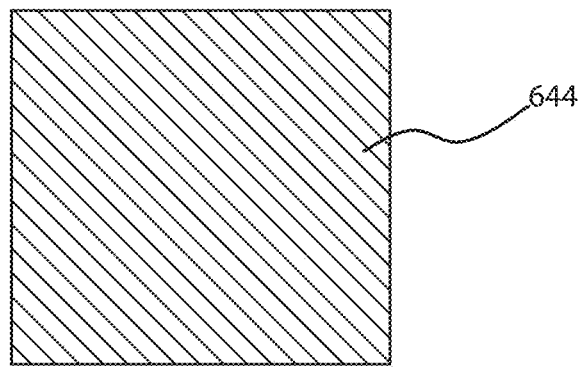
FIG. 6A-6C are schematic diagrams of data usage in accordance with various embodiments herein.
Figure 6B:
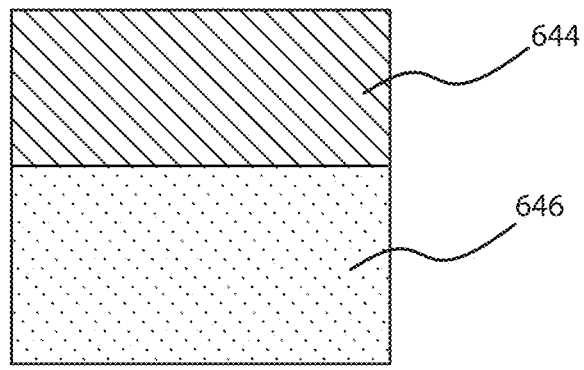
Figure 6C:
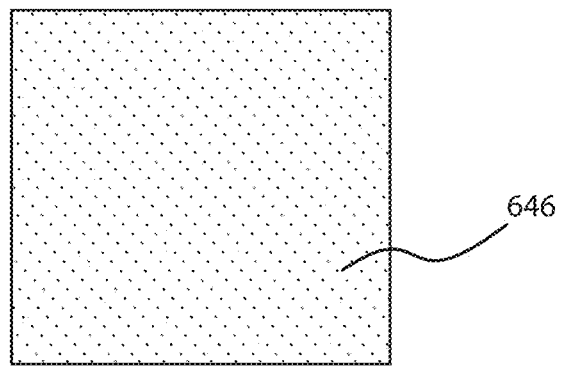

In various embodiments, the data used to generate/update the model, function or equation can change over time, such as shown in FIGS. 6A-6C. FIGS. 6A-6C show schematics of data being used for the baseline or model in accordance with various embodiments herein. The model, function or equation can be used to predict the potassium levels based on cardiac electrogram data can be unique to the patient. The baseline can include patient specific data, non-patient specific data, or a combination of patient and non-patient specific data.

FIG. 6A represents the data usage for an initial model for a patient. In some embodiments, an initial model can include non-specific patient data 644, such as data that does not specifically belong to the patient that is currently being monitored. In some embodiments, the non-specific patient data include or be derived from a pool of patients. In some embodiments, the pool of patients can include similar characteristics to the patient currently being monitored, such as similar age, race, gender, cardiac performance (e.g. blood pressure or heart rate), health status (e.g. diseases or conditions), lifestyle, or geographical location.

Over time, more patient-specific data can be gathered and used to update or otherwise change the model, function or equation. FIG. 6B shows a schematic diagram for data usage in a model for a patient using a combination of at least some patient specific data 646 and some non-specific patient data 644. The patient specific data 646 can include previously measured data, such as gathered cardiac electrogram data in combination with measured potassium levels from in vitro assays or other definitive sources, from the patient being monitored who the model is developed for. In some embodiments, the amount of patient specific data can increase as additional cardiac electrogram data is gathered in combination with results from in vitro assays or other definitive potassium concentration data.

In some cases, the model, function or equation used for a specific patient may eventually be generated or derived entirely from data that is for that specific patient. The FIG. 6C shows a schematic for data usage in a model for a patient using all patient specific data 646. In some embodiments, after one or more occasions of cardiac electrogram data being gathered in combination with results from an in vitro assay, the systems or methods described herein in can exclusively use the known information that is specific to the patient being monitored.

In some embodiments, as time progresses, and additional patient specific data is obtained, less relevant, accurate or simply older patient data can be discarded. In some embodiments, the oldest patient specific data is discarded as new data is gathered. In some embodiments, the least relevant patient specific data can be discarded, such as data that was gathered during a period that is no longer representative of the patient's current health status, such as a change in heart performance, or the development or resolution of a disease or condition.

System and Devices

Figure 7:
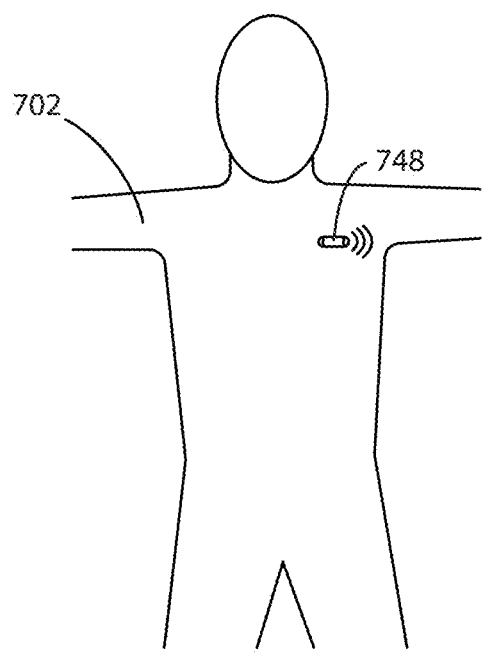
FIG. 7 is a schematic diagram of an implantable medical device within a patient in accordance with various embodiments herein.

Referring now to FIG. 7, a schematic view is shown of an implantable medical device 748 consistent with various embodiments herein. In some embodiments, the implantable medical device 748 can include an implantable loop recorder, implantable monitor device, or the like. The implantable medical device 748 can be implanted within the body of a patient 702. Various implant sites can be used including areas on the limbs, the upper torso, the abdominal area, and the like.

Figure 8:
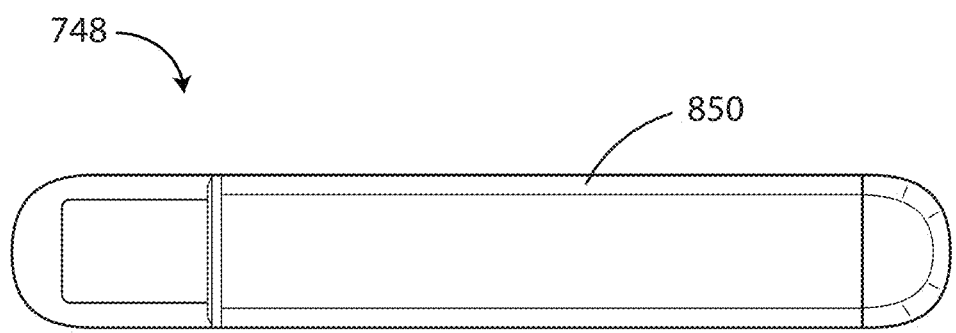
FIG. 8 is a schematic view of an implantable device in accordance with various embodiments herein.

In reference now to FIG. 8 a schematic view of an implantable device 748 is shown in accordance with various embodiments herein. In some embodiments, systems described herein can include an implantable device 748. In some embodiments, the implantable device 748 can include a monitoring device or a pacing device. The implantable device 748 can include two or more electrodes which can be configured to gather cardiac electrogram data.

In some embodiments, the implantable medical device 748 can include a housing 850. The implantable medical device 748 can include a control circuit disposed in the housing 850. The implantable medical device 748 can include an electric field sensor channel interface in electrical communication with the control circuit.

The control circuit can be configured to conduct or perform the methods described herein. In some embodiments, the control circuit can be configured to separate cardiac electrogram data received from the electric field sensor into discrete subunits including a T-wave. The control circuit can also be configured to align T-waves to create aligned discrete subunits. Additionally, the control circuit can be configured to average the aligned discrete subunits to generate an average T-wave for the cardiac electrogram data. Further, the control circuit can be configured to determine a serum potassium change using the average T-wave for the cardiac electrogram data and a predetermined model relating T-wave morphology with serum potassium magnitudes.

Figure 9:
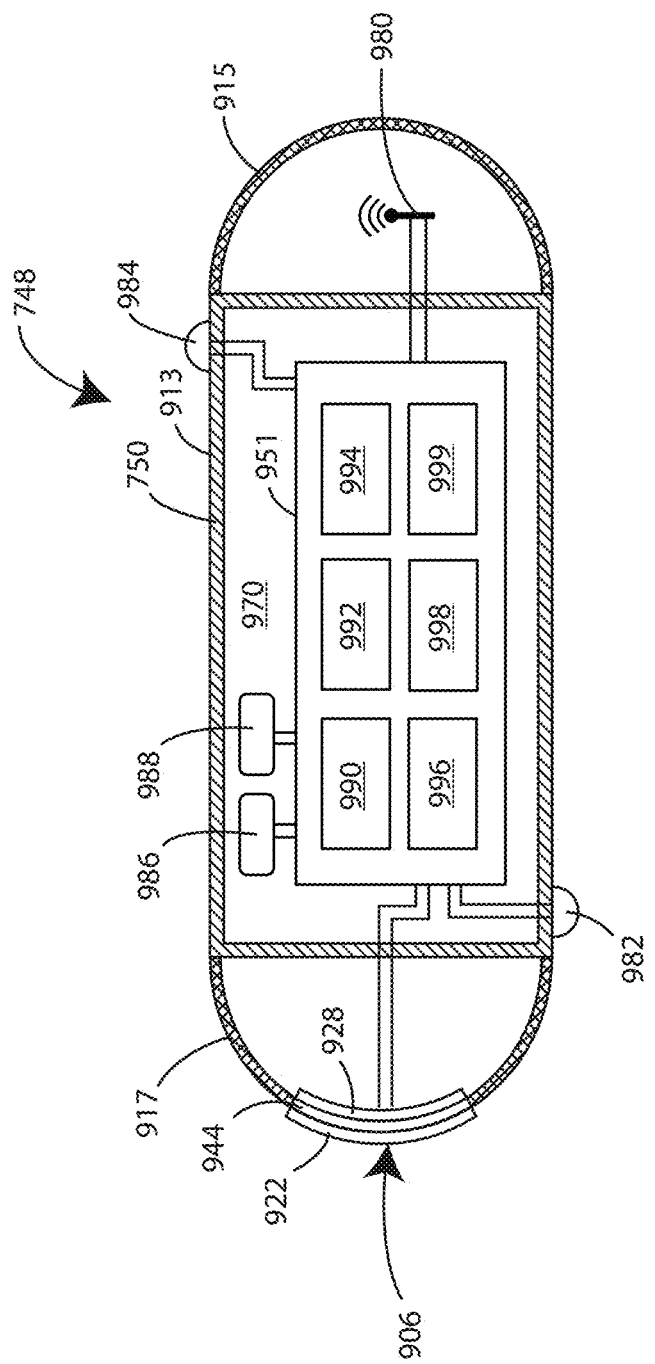
FIG. 9 is a schematic cross-sectional view of an implantable medical device in accordance with various embodiments herein.

Referring now to FIG. 9, a schematic cross-sectional view of the implantable medical device 748 is shown in accordance with various embodiments herein. The implantable medical device 748 includes a housing 750. The housing 750 of the implantable medical device 748 can include various materials such as metals, polymers, ceramics, and the like. In some embodiments, the housing 750 can be a single integrated unit. In other embodiments, the housing 750 can include a main segment 913 along with appendage segments 915 and 917. In one embodiment, the housing 750, or one or more portions thereof, is formed of titanium. In some embodiments, one or more segments of the housing 750 can be hermetically sealed. In some embodiments, the main segment 913 is formed of a metal and the appendage segments 915 and 917 are formed from a polymeric material.

The housing 750 defines an interior volume 970 that in some embodiments is hermetically sealed off from the area 972 outside of the device 748. The device 748 can include circuitry 951. The circuitry 951 can include various components, such as components 990, 992, 994, 996, 998, and 999. In some embodiments, these components can be integrated and in other embodiments these components can be separate. In some embodiments, the components can include one or more of a microprocessor, memory circuitry (such as random access memory (RAM) and/or read only memory (ROM)), recorder circuitry, telemetry circuitry, sensor interface circuitry, power supply circuitry (which can include one or more batteries), normalization circuitry, control circuitry, and the like. In some embodiments, the circuitry can be hardwired to execute various functions while in other embodiments, the circuitry can be implemented as instructions executing on a microprocessor or other computation device.

The implantable medical device 748 can include, for example, an electrical field sensor that is configured to generate a signal corresponding to cardiac electric fields. The electrical field sensor can include a first electrode 982 and a second electrode 984. In some embodiments, the housing 750 itself can serve as an electrode. The electrodes can be in communication with the electrical field sensor. The electrical field sensor can include a circuit in order to measure the electrical potential difference (voltage) between the first electrode 982 and the second electrode 984. The implantable medical device 748 can also include an antenna 980, to allow for unidirectional or bidirectional wireless data communication.

The implantable medical device 748 can also include an additional sensor 906. In the embodiment shown in FIG. 9, the sensor is an optical sensor. However, many other sensors are contemplated herein. The additional sensor 906 can specifically include a sensing element 922, an optical window 944, and an electro-optical module 928. The electro-optical module 928 can be in electrical communication with the circuitry 951 within the interior volume 970, and in some embodiments, the circuitry 951 is configured to selectively activate the sensor 906. The sensor 906 can be configured to be chronically implanted.

In some embodiments the chemical sensing element 922 is located in a fluid such as blood, interstitial fluid, urine, lymph or chyle and senses analytes in a fluid. In other embodiments, the chemical sensing element 922 is located in a solid tissue such as muscle, fat, bone, bone marrow, organ tissues (e.g. kidney, liver, brain, lung, etc.) and senses analytes in a solid tissue.

Figure 10:
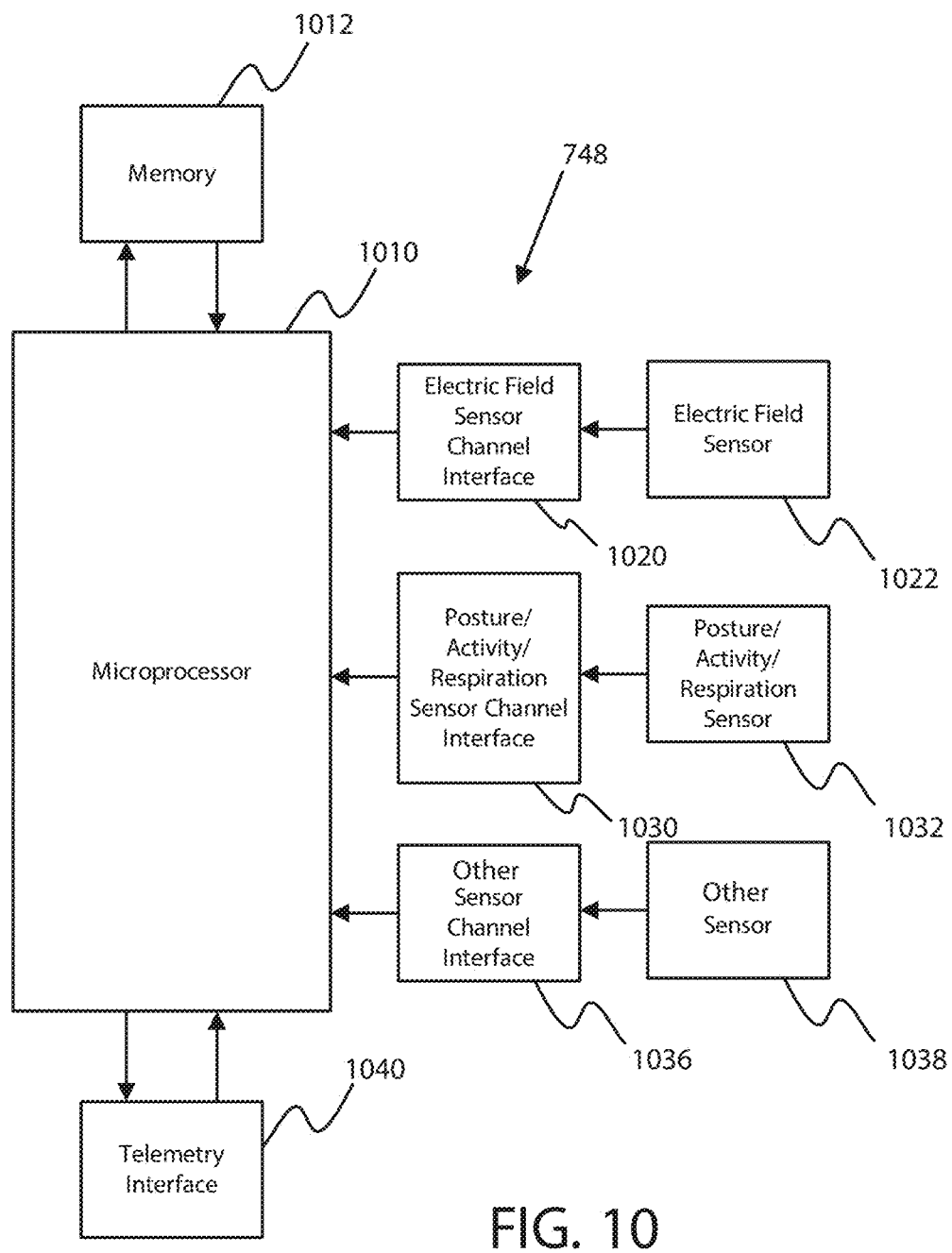
FIG. 10 is a schematic diagram of components of an implantable medical device in accordance with various embodiments herein.

Elements of various embodiments of an implantable medical device are shown in FIG. 10. However, it will be appreciated that some embodiments can include additional elements beyond those shown in FIG. 10. In addition, some embodiments may lack some elements shown in FIG. 10. The medical device 748 can gather information through one or more sensing channels. A microprocessor 1010 can communicate with a memory 1012 via a bidirectional data bus. In various embodiments, the microprocessor 1010 (or another electronic component with processing capabilities) can serve as a control circuit. The memory 1012 can include read only memory (ROM) or random access memory (RAM) for program storage and RAM for data storage.

The implantable medical device can include one or more electrodes 1022 and an electric field sensor channel interface 1020 which can communicate with a port of microprocessor 1010. The implantable medical device can also include one or more posture, activity, or respiration sensors 1032 and a posture/activity/respiration sensor channel interface 1030 which can communicate with a port of microprocessor 1010. The implantable medical device can also include an additional sensor 1038 and a sensor channel interface 1036 which can communicate with a port of microprocessor 1010. The channel interfaces 1020, 1030 and 1036 can include various components such as analog-to-digital converters for digitizing signal inputs, sensing amplifiers, registers which can be written to by the control circuitry in order to adjust the gain and threshold values for the sensing amplifiers, and the like. A telemetry interface 1040 is also provided for communicating with external devices such as a programmer, a home-based unit and/or a mobile unit (e.g., a cellular phone).

Although the posture, activity, or respiration sensors 1032 are shown as part of medical device 748 in FIG. 10 it is realized that in some embodiments one or more of the posture, activity, or respiration sensors could be separate from medical device 748. In various embodiments one or more of the posture, activity, or respiration sensors are within another implanted medical device communicatively coupled to medical device 748 via telemetry interface 1040. In various embodiments one or more of the posture, activity, or respiration sensors are external to the body and are coupled to medical device 748 via telemetry interface 1040.

Figure 11:
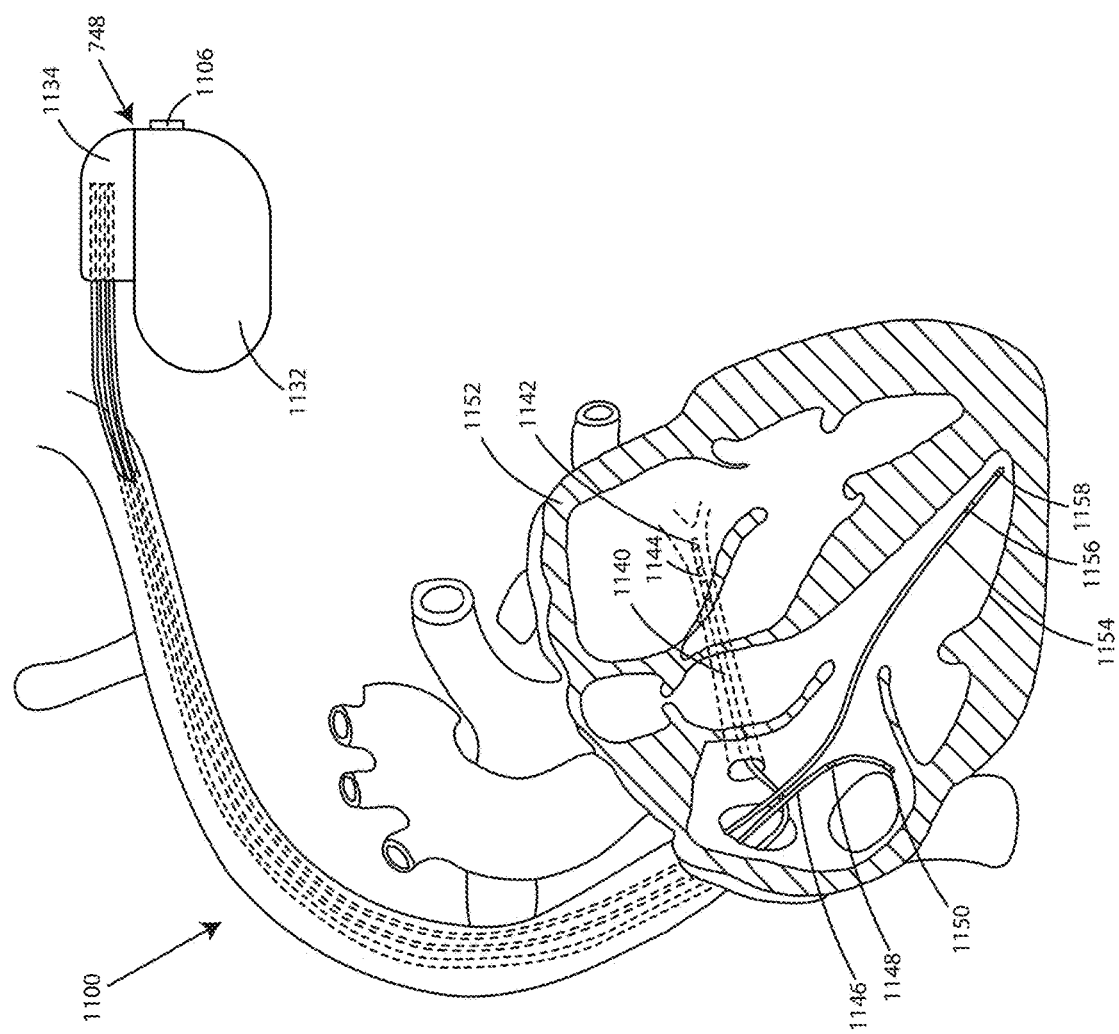
FIG. 11 is a schematic view of an implantable medical system in accordance with various embodiments herein.

Referring now to FIG. 11, a schematic view is shown of an implantable medical system 1100. The implantable medical system 1100 includes an implantable medical device 748 and one or more stimulation leads 1140, 1146, and 1154. In various embodiments, the implantable medical device 748 can include a cardiac rhythm management device, such as a pacemaker, a cardiac resynchronization therapy (CRT) device, a remodeling control therapy (RCT) device, a cardioverter/defibrillator, or a device providing two or more of these therapies. In some embodiments, the implantable medical device 748 can be, or include, a neurological stimulation device.

The implantable medical device 748 can include a pulse generator housing 1132 and a header 1134. The term "pulse generator housing" as used herein shall refer to the part or parts of an implanted medical device, such as a cardiac rhythm management device or a neurological therapy device, containing the power source and circuitry for delivering pacing therapy, electrical stimulation, and/or shock therapy. Together, the pulse generator housing 1132, the contents therein, and the header 1134 can be referred to as a pulse generator. It will be appreciated that embodiments herein can also be used in conjunction with implantable medical devices that may lack pulse generators such as monitoring devices and drug delivery devices.

In FIG. 11, the proximal ends of the stimulation leads 1140, 1146, and 1154 are disposed within the header 1134. The stimulation leads 1140, 1146, and 1154 can pass to the heart 1152 transvenously. In this view, stimulation lead 1140 passes into the coronary venous system, stimulation lead 1146 passes into the right atrium, and stimulation lead 1154 passes into the right ventricle. However, it will be appreciated that stimulation leads can be disposed in various places within or around the heart. Stimulation lead 1140 includes a tip electrode 1142 and a ring electrode 1144. Stimulation leads 1146 and 1154 also include tip electrodes 1150 and 1158 and ring electrodes 1148 and 1156, respectively. It will be appreciated that stimulation leads can include different numbers of electrodes. For example, in some embodiments, a stimulation lead may only include a single electrode and in some embodiments a stimulation lead may include more than two electrodes. Depending on the configuration, the stimulation leads can provide electrical and/or optical communication between the distal ends of the stimulation leads and the pulse generator. In operation, the pulse generator may generate pacing pulses or therapeutic shocks which are delivered to the heart 1152 via the electrodes of the stimulation leads. In many embodiments, the stimulation leads include a material that is electrically conductive in order to deliver the pacing pulses or therapeutic shocks.

Figure 12:
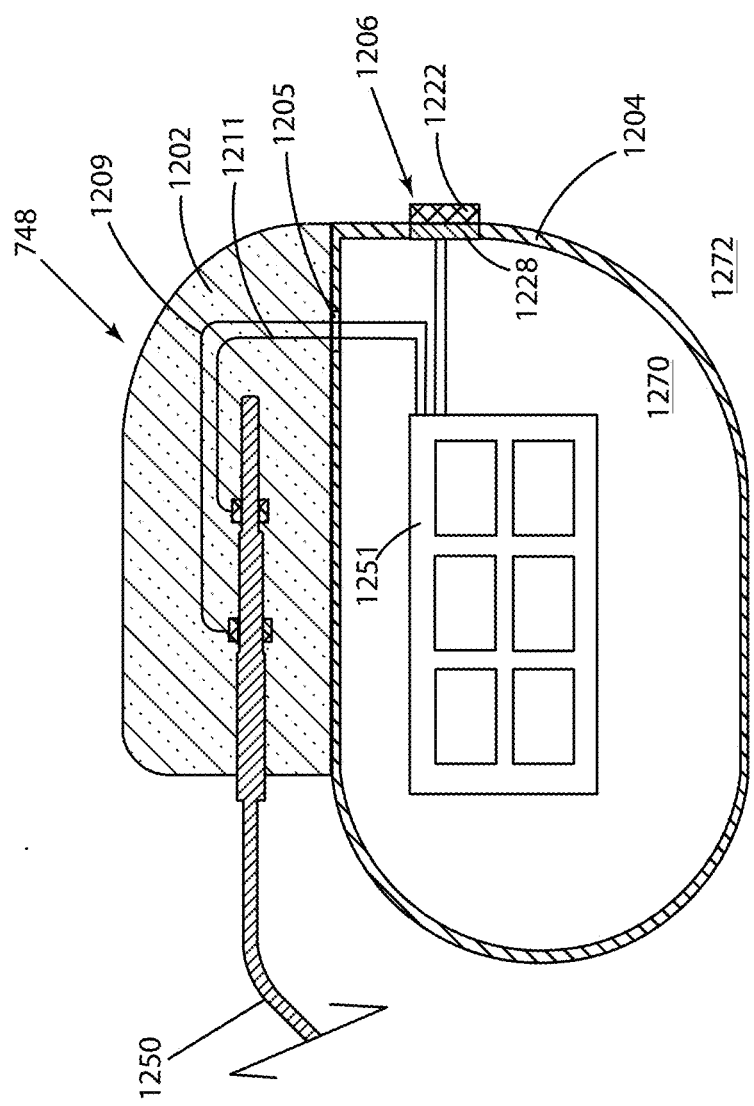
FIG. 12 is a schematic cross-sectional view of an implantable medical device in accordance with various embodiments herein.

The implantable medical system 1100 can also be configured to sense electrical activity of the heart. By way of example, the implantable medical system 1100 can include an electrical field sensor (such as shown in FIG. 12 as part of circuitry 1251). Specifically, the implantable medical system 1100 can use one or more electrodes, such as the electrodes on the stimulation leads 1142, 1144, 1148, 1150, 1156, and/or 1158, in order to sense electrical activity of the heart, such as a time-varying electrical potential. In some embodiments, the pulse generator housing 1132 can serve as an electrode for purposes of sensing electrical activity and/or delivering electrical stimulation. The implantable medical system 1100 can also include a sensor 1106.

Referring now to FIG. 12, a schematic cross-sectional view of an implantable medical device 748 is shown in accordance with various embodiments herein. The implantable medical device 748 includes a header assembly 1202 and a housing 1204. The housing 1204 of the implantable medical device 748 can include various materials such as metals, polymers, ceramics, and the like. In one embodiment, the housing 1204 is formed of titanium. The header assembly 1202 can be coupled to one or more electrical stimulation leads 1250. The header assembly 1202 serves to provide fixation of the proximal end of one or more leads and electrically couples the leads to components within the housing 1204. The header assembly 1202 can be formed of various materials including metals, polymers, ceramics, and the like.

The housing 1204 defines an interior volume 1270 that is hermetically sealed off from the volume 1272 outside of the device 748. Various electrical conductors 1209, 1211 can pass from the header assembly 1202 through a feed-through structure 1205, and into the interior volume 1270. As such, the conductors 1209, 1211 can serve to provide electrical communication between the electrical stimulation lead 1250 and circuitry 1251 disposed within the interior volume 1270 of the housing 1204. The circuitry 1251 can include various components such as a microprocessor or control circuit, memory (such as random access memory (RAM) and/or read only memory (ROM)), a telemetry module, electrical field sensor and stimulation circuitry, a power supply (such as a battery), and an optical sensor interface channel, amongst others.

The implantable medical device 748 can incorporate, for example, an electrical field sensor that is configured to generate a signal corresponding to cardiac electric fields. The electrical field sensor can include a first electrode and a second electrode. The electrodes of the electrical field sensor can be the same electrodes used to provide electrical stimulation (such as referred to with respect to FIG. 11) or can be different electrodes. In some embodiments, one or more electrodes can be mounted on one or more electrical stimulation leads 1250. In some embodiments, the housing 1204 can serve as an electrode. The electrodes can be in communication with the electrical field sensor and stimulation circuitry. The electrical field sensor can include a circuit (such as within circuitry 1251) in order to measure the electrical potential difference (voltage) between the first electrode and the second electrode.

The implantable medical device 748 can also include a sensor 1206. In the embodiment shown in FIG. 12, the sensor can be a potentiometric sensor. The sensor 1206 can include a receptor module 1222, and a transducer module 1228. The transducer module 1228 can be in electrical communication with the circuitry 1251 within the interior volume 1270, and in some embodiments, the circuitry 1251 is configured to selectively activate the sensor. The sensor 1206 can be configured to be chronically implanted.

Figure 13:
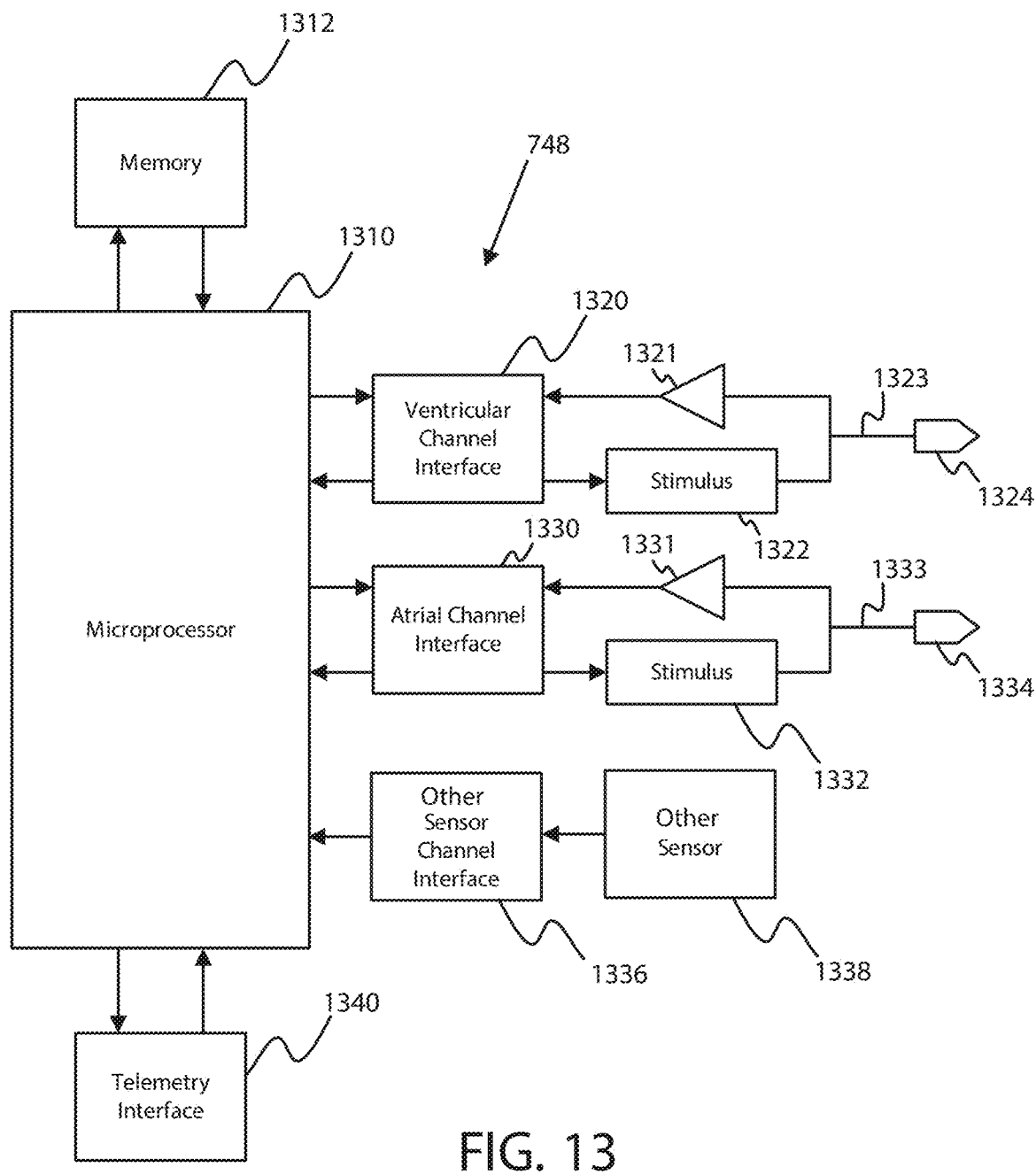
FIG. 13 is a schematic diagram of components of an implantable medical device in accordance with various embodiments herein.

Elements of some embodiments of an implantable medical device are shown in FIG. 13. However, it will be appreciated that some embodiments can include additional elements beyond those shown in FIG. 13. In addition, some embodiments may lack some elements shown in FIG. 13.

The medical device 748 can sense cardiac events through one or more sensing channels and outputs pacing pulses to the heart via one or more pacing channels in accordance with a programmed pacing mode. A microprocessor 1310 can be part of a control circuit and can communicate with a memory 1312 via a bidirectional data bus. The memory 1312 typically comprises read only memory (ROM) or random access memory (RAM) for program storage and RAM for data storage.

The implantable medical device can include atrial sensing and pacing channels comprising at least a first electrode 1334, lead 1333, sensing amplifier 1331, output circuit 1332, and an atrial channel interface 1330 which can communicate bidirectionally with a port of microprocessor 1310. In this embodiment, the device also has ventricular sensing and pacing channels comprising at least a second electrode 1324, lead 1323, sensing amplifier 1321, output circuit 1322, and ventricular channel interface 1320. For each channel, the same lead and electrode are used for both sensing and pacing. The channel interfaces 1320 and 1330 include analog-to-digital converters for digitizing sensing signal inputs from the sensing amplifiers and registers which can be written to by the control circuitry in order to output pacing pulses, change the pacing pulse amplitude, and adjust the gain and threshold values for the sensing amplifiers. The implantable medical device can also include an additional sensor 1338 and a sensor channel interface 1336. A telemetry interface 1340 is also provided for communicating with an external programmer.

Methods

Figure 14:
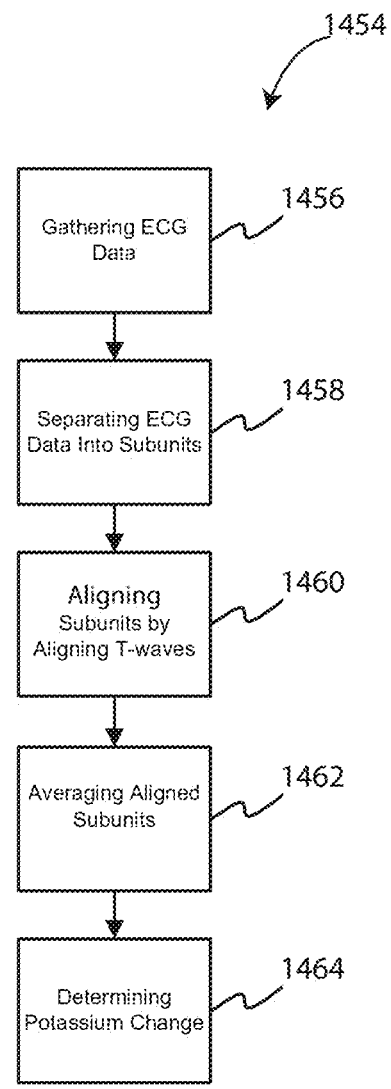
FIG. 14 is a flow chart showing a method in accordance with various embodiments herein.

FIG. 14 shows a flow chart showing a method 1454 in accordance with various embodiments herein. The method 1454 for monitoring serum potassium in a patient can include gathering cardiac electrogram data from the patient using two or more electrodes 1456. The method 1454 can include separating the cardiac electrogram data into discrete subunits including a T-wave 1458. The method 1454 can also include aligning subunits by aligning T-waves to create aligned discrete subunits 1460. The method 1454 can further include averaging the aligned discrete subunits to generate an average T-wave for the cardiac electrogram data 1462. Additionally, the method can include determining a serum potassium change using the average T-wave (or the T-wave delta value compared with a baseline T-wave value) for the cardiac electrogram data and a predetermined model relating T-wave morphology or parameters or T-wave delta values with serum potassium magnitudes 1464.

In some embodiments, determining a serum potassium magnitude can include calculating an average T-wave delta (change) of the patient by comparing the average T-wave for the cardiac electrogram data against a previously determined baseline average T-wave for the patient; and determining a serum potassium magnitude using the average T-wave change for the cardiac electrogram data and a predetermined model relating T-wave morphology with serum potassium magnitudes.

Aspects may be better understood with reference to the following example. This example is intended to be representative of specific embodiments, but is not intended as limiting the overall scope of embodiments herein.

EXAMPLES

Example 1

T-Wave Changes and Serum Potassium Changes in a Group of Dialysis Patients

Cardiac electrogram data was recorded for a group of dialysis patients both before dialysis and after dialysis. In a normal dialysis treatment, the patient has his/her blood drawn prior to the treatment. This blood was used to establish a known level of potassium in the patient's serum. It is relatively common for dialysis patients to have their serum potassium concentrations change as a result of dialysis and thus they represented an ideal group to evaluate T-wave changes based on potassium change.

Figure 15:
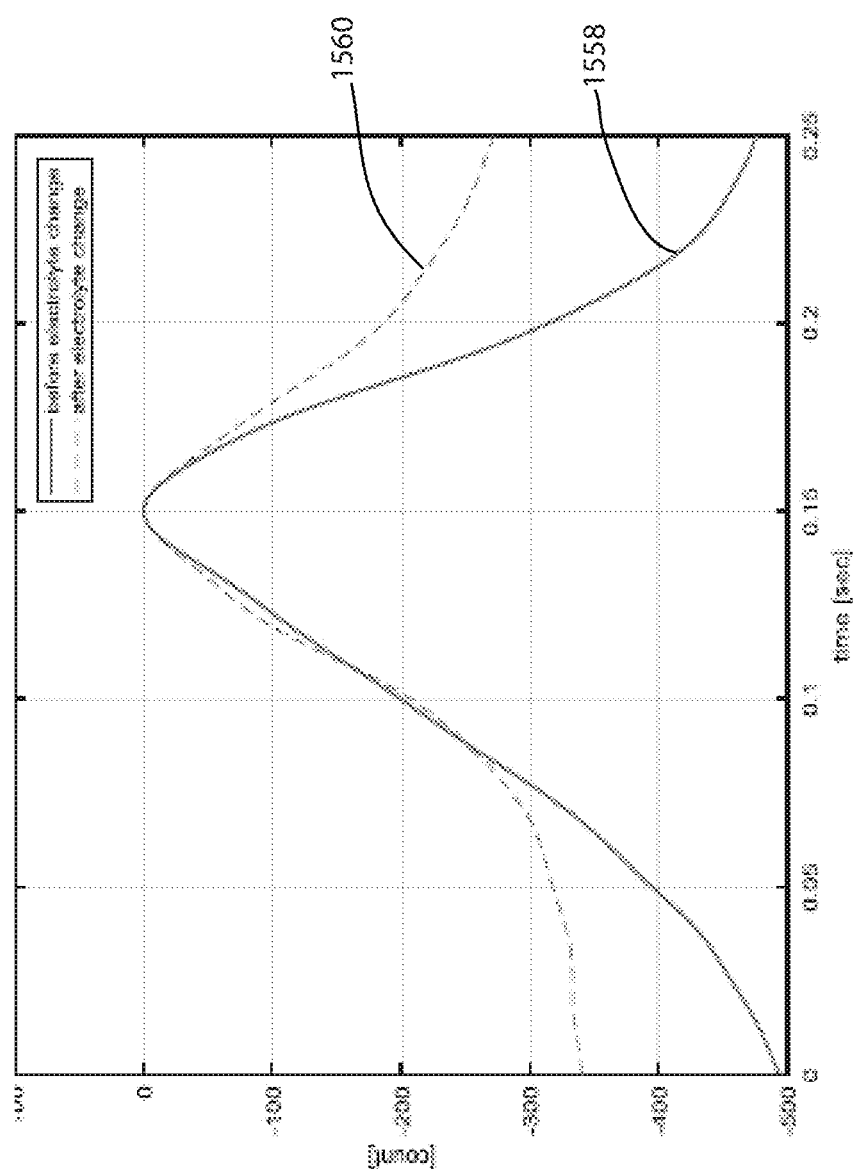
FIG. 15 is a graph of averaged T-waves as described in Example 1 herein.

Cardiac electrogram data was recorded for each patient over 1 minute before dialysis and over 1 minute after dialysis. The cardiac electrogram data was separated into subunits. Each subunit included a T-wave. The T-waves were averaged. FIG. 15 shows the average T-wave before dialysis 1558 and the average T-wave after dialysis. FIG. 15 specifically shows the before and after T-wave averages for a single patient. Similar data sets were created for every patient in the testing pool.

Figure 16:
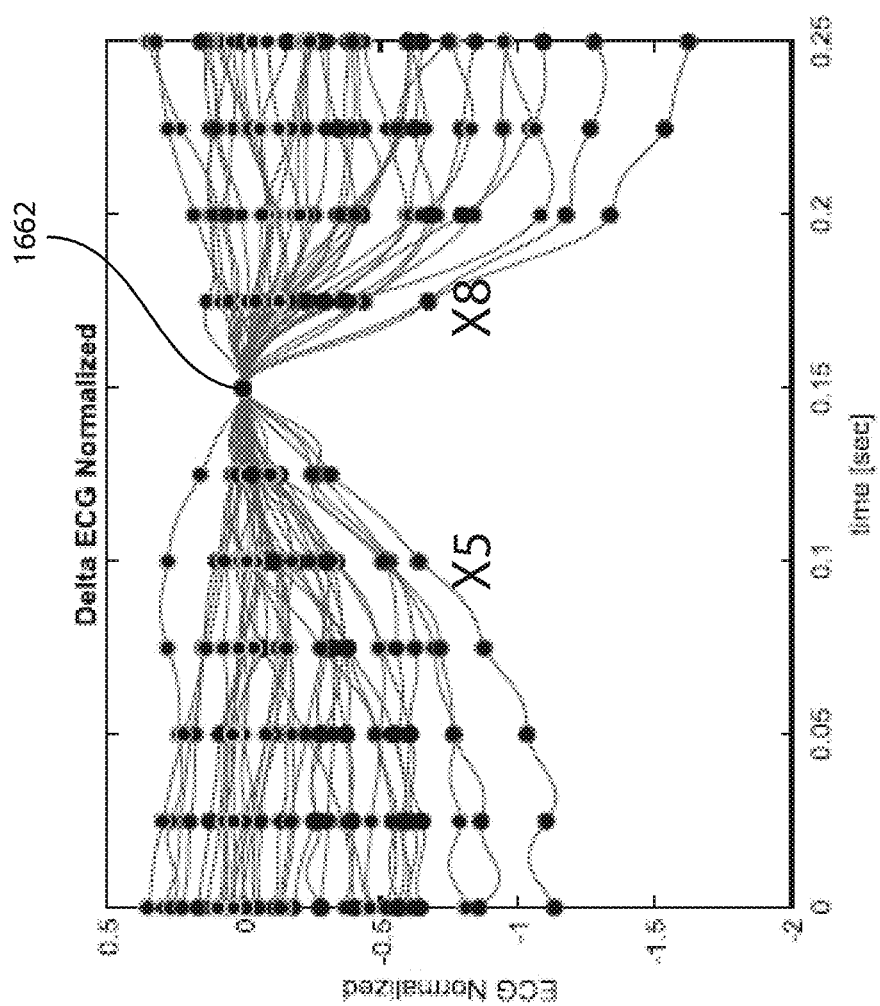
FIG. 16 is a graph showing normalized T-wave changes over baseline values as described in Example 1 herein.

Delta plots of T-wave changes due to potassium change were generated (FIG. 16). For each patient, a normalized average T-wave graph was created using T-wave amplitude (e.g., the data for every patient was normalized versus the other patients based on T-wave amplitude). Next, that average T-wave (normalized before dialysis) was subtracted from the after-dialysis T-wave (normalized after dialysis) to create a T-wave delta plot that was normalized. Each line in FIG. 16 represents one of the patients. The delta plot was resampled to create a limited amount of less correlated data points that would then be used in regression analysis. Point 1662 in FIG. 16 represents the peaks of the T-waves, around which the T-waves from various patients were aligned.

All of the resampled points for all patients were evaluated using a regression analysis tool (JMP). Certain points were identified by the regression tool as the most relevant for regression fit (X5 and X8 identified in FIG. 16). The equation generated by the analysis was: $\Delta\hat{K}=2.73-5.46*X5+3.68*X8$. Details of the regression analysis are shown below in Table 1.

TABLE 1

| Summary of Fit | |
| --- | --- |
| Rsquare | 0.379192 |
| Rsquare Adj | 0.340392 |
| Root Mean Square Error | 0.916762 |
| Mean of Response | 3.022857 |
| Observations (or Sum Wgts) | 35 |

| Analysis of Variance | | | | |
| --- | --- | --- | --- | --- |
| Source | DF | Sum of Squares | Mean Square | F Ratio |
| Model | 2 | 16.427257 | 8.21363 | 9.7729 |
| Error | 32 | 26.894458 | 0.84045 | Prob > F |
| C. Total | 34 | 43.321714 | | 0.0005 |

| Parameter Estimates | | | | |
| --- | --- | --- | --- | --- |
| Term | Estimate | Std Error | t Ratio | Prob > \|t\| |
| Intercept | 2.732675 | 0.205679 | 13.29 | <.0001 |
| Var2_5 | −5.45749 | 1.40447 | −3.89 | 0.0005 |
| Var2_8 | 3.676602 | 1.616169 | 2.27 | 0.0298 |

Figure 17:
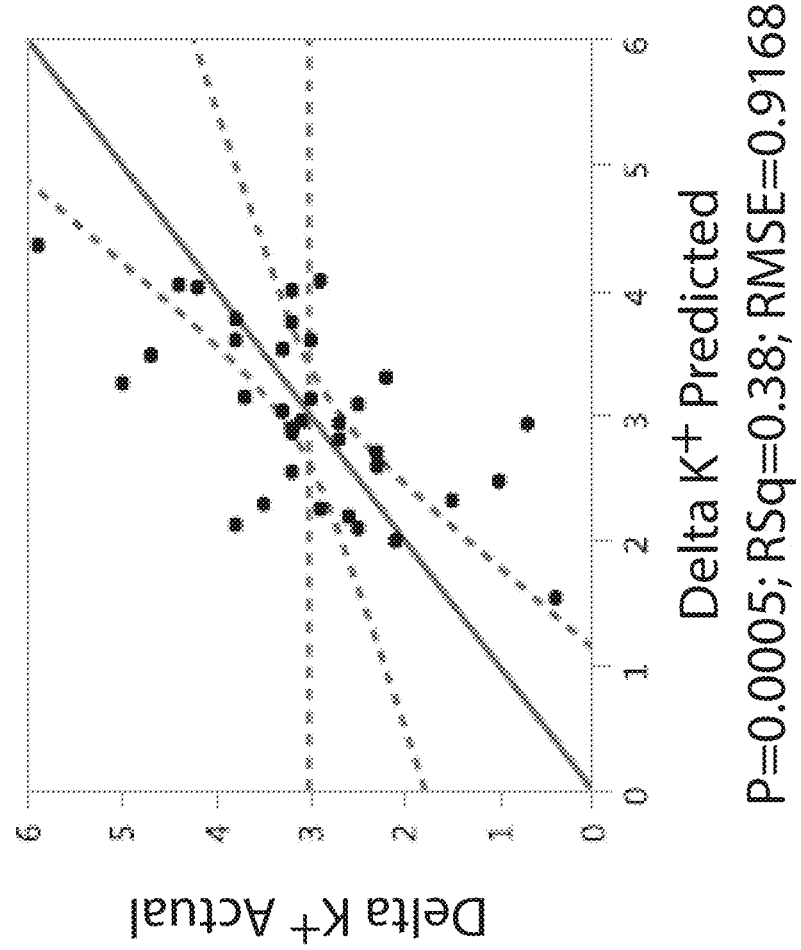
FIG. 17 is a plot of actual vs. predicted change of potassium levels as described in Example 1 herein.

The results of the regression tool were plotted as shown in FIG. 17. FIG. 17 specifically shows a plot of the actual change in potassium levels compared to the predicted change in potassium levels. This example shows that embodiments herein can be used to predict potassium concentrations based on cardiac electrogram data with significant accuracy.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method for monitoring serum potassium in a patient comprising:
    gathering cardiac electrogram data from the patient using an implantable medical device having two or more electrodes;
    separating, using the implantable medical device comprising a control circuit configured to separate, the cardiac electrogram data into discrete subunits including a T-wave;
    aligning, using the implantable medical device comprising a control circuit configured to align, T-waves to create aligned discrete subunits;
    averaging, using the implantable medical device comprising a control circuit configured to average, the aligned discrete subunits to generate an average T-wave for the cardiac electrogram data;
    determining, using the implantable medical device comprising a control circuit configured to determine, a serum potassium value using the average T-wave for the cardiac electrogram data and a predetermined model relating T-wave values with serum potassium magnitudes;
    comparing the serum potassium value to a threshold value; and
    sending a notification signal from the implantable medical device through a telemetry interface of the medical device to an external device based on the comparison of the serum potassium value with the threshold value;
    wherein determining a serum potassium value using the average T-wave for the cardiac electrogram data and a predetermined model relating T-wave morphology with serum potassium values comprises:
        calculating an average T-wave change of the patient by comparing the average T-wave for the cardiac electrogram data against a previously determined baseline average T-wave for the patient; and
        determining a serum potassium value using the average T-wave change for the cardiac electrogram data and a predetermined model relating T-wave change values with serum potassium values.

2. The method of claim 1, further comprising periodically updating the predetermined model by evaluating an average T-wave of the patient corresponding to a serum potassium concentration of the patient measured in vitro.

3. The method of claim 2, wherein the predetermined model is only updated after at least two separate in vitro measurements are made.

4. The method of claim 2, wherein the predetermined model is only updated after at least 21 days after a device implant.

5. The method of claim 1, wherein gathering cardiac electrogram data from the patient using two or more electrodes is performed with an implanted device.

6. The method of claim 1, wherein the predetermined model relating T-wave values with serum potassium values represents the output of at least one of a regression analysis and a machine learning analysis.

7. The method of claim 6, wherein the inputs for the regression analysis or machine learning analysis include previous cardiac electrogram data for the patient.

8. The method of claim 1, wherein each discrete subunit including a T-wave comprises cardiac electrogram data spanning a time span of at least 0.15 seconds.

9. The method of claim 1, wherein each discrete subunit including a T-wave comprises cardiac electrogram data spanning a time span that is user programmable.

10. The method of claim 1, wherein the number of discrete subunits that are averaged is at least about 10 subunits.

11. The method of claim 1, wherein the cardiac electrogram data spans at least 10 minutes.

12. The method of claim 1, wherein aligning T-waves is selected from the group consisting of aligning peaks of the T-waves, aligning starting points of the T-waves, aligning ending points of the T-waves, aligning midpoints of the T-waves, aligning a single point of the T-waves, or aligning two or more points of the T-waves.

13. The method of claim 1, further comprising discarding discrete subunits representing statistical outliers.

14. The method of claim 13, wherein statistical outliers are evaluated by evaluating at least one of R to R variability and R to T variability.

15. The method of claim 1, further comprising sending a prompt to an external patient device through the telemetry interface, wherein the prompt directs the patient to take a specific action prior to gathering cardiac electrogram data from the patient.

16. The method of claim 1, wherein gathering cardiac electrogram data from the patient starts based on at least one of
    the patient assuming a particular posture;
    a particular time of day; or
    activity below a predefined threshold.

17. The method of claim 1, further comprising storing a new baseline T-wave value of the patient if the T-wave is stable over at least a threshold period of time.

18. The method of claim 17, the threshold period of time comprising at least 30 days.

19. An implantable medical device comprising:
a housing;
a control circuit disposed in the housing;
a telemetry interface in electrical communication with the control circuit;
an electric field sensor channel interface in electrical communication with the control circuit;
wherein the control circuit is configured to
  separate cardiac electrogram data received from the electric field sensor into discrete subunits including a T-wave;
  align the subunits using the T-waves thereof to create aligned discrete subunits;
  average the aligned discrete subunits to generate an average T-wave for the cardiac electrogram data;
  determine a serum potassium value using the average T-wave for the cardiac electrogram data and a predetermined model relating T-wave values with serum potassium values;
  compare the serum potassium value to a threshold value; and
  send a notification signal from the implantable medical device through the telemetry interface to an external device based on the comparison of the serum potassium value with the threshold value;
wherein determining a serum potassium value using the average T-wave for the cardiac electrogram data and a predetermined model relating T-wave morphology with serum potassium values comprises:
  calculating an average T-wave change of the patient by comparing the average T-wave for the cardiac electrogram data against a previously determined baseline average T-wave for the patient; and
  determining a serum potassium value using the average T-wave change for the cardiac electrogram data and a predetermined model relating T-wave change values with serum potassium values.

20. The method of claim 1, further comprising:
in response to the comparison of the serum potassium value with the threshold value, performing a confirmation test to quantify a serum potassium concentration.

* * * * *